(12) United States Patent
Pedersen et al.

(10) Patent No.: US 6,171,297 B1
(45) Date of Patent: Jan. 9, 2001

(54) RADIOPAQUE CATHETER TIP

(75) Inventors: Allen R. Pedersen, Bloomington; Dennis A. Peiffer, Maple Grove, both of MN (US)

(73) Assignee: Schneider (USA) Inc, Plymouth, MN (US)

( * ) Notice: Under 35 U.S.C. 154(b), the term of this patent shall be extended for 0 days.

(21) Appl. No.: 09/107,734

(22) Filed: Jun. 30, 1998

(51) Int. Cl.[7] ................................................. A61M 25/00
(52) U.S. Cl. ............................................ 604/527; 604/264
(58) Field of Search ........................... 604/264, 523–527, 604/529

(56) References Cited

U.S. PATENT DOCUMENTS

| | | | |
|---|---|---|---|
| 4,447,239 | * 5/1984 | Krutten | 604/282 |
| 4,516,972 | 5/1985 | Samson | 604/282 |
| 4,531,943 | 7/1985 | Van Tassel | 604/280 |
| 4,547,193 | 10/1985 | Rydell | 604/282 |
| 4,636,346 | 1/1987 | Gold | 264/139 |
| 4,646,742 | 3/1987 | Packard | 128/344 |
| 4,655,771 | 4/1987 | Wallsten | 623/1 |
| 4,806,182 | 2/1989 | Rydell | 156/211 |
| 4,898,591 | 2/1990 | Jang | 604/282 |
| 5,019,057 | * 5/1991 | Truckai | 604/527 |
| 5,037,404 | 8/1991 | Gold | 604/282 |
| 5,041,100 | 8/1991 | Rowland | 604/265 |
| 5,045,072 | 9/1991 | Castillo et al. | 604/280 |
| 5,057,092 | 10/1991 | Webster, Jr. | 604/282 |
| 5,063,935 | * 11/1991 | Gambale | 128/657 |
| 5,171,232 | 12/1992 | Castillo et al. | 604/280 |
| 5,221,270 | 6/1993 | Parker | 604/282 |
| 5,240,537 | 8/1993 | Bodicky | 156/244 |
| 5,265,622 | * 11/1993 | Barvere | 128/72 |
| 5,312,356 | 5/1994 | Engelson | 604/164 |
| 5,364,357 | 11/1994 | Aase | 604/96 |
| 5,403,292 | 4/1995 | Ju | 604/282 |
| 5,405,380 | 4/1995 | Gianotti | 623/1 |
| 5,538,513 | 7/1996 | Okajima | 604/282 |
| 5,545,151 | 8/1996 | O'Connor | 604/282 |
| 5,599,325 | 2/1997 | Ju | 604/282 |
| 5,628,787 | 5/1997 | Mayer | 623/1 |
| 5,630,806 | * 5/1997 | Inagaki et al. | 604/529 |
| 5,630,840 | 5/1997 | Mayer | 623/1 |
| 5,728,063 | * 3/1998 | Preissman et al. | 604/96 |
| 5,836,926 | 11/1998 | Peterson et al. | 604/282 |
| 5,843,032 | 12/1998 | Kastenhofer | 604/96 |
| 5,906,606 | * 5/1999 | Chee et al. | 604/527 |

FOREIGN PATENT DOCUMENTS

| | | | |
|---|---|---|---|
| 0 249 338 A2 | 5/1987 | (EP) | A62M/25/00 |
| 0 249 338 A2 | 12/1987 | (EP) | A61M/25/00 |
| 0 358 117 A2 | 3/1990 | (EP) | A61M/29/02 |
| 0 369 383 A2 | 5/1990 | (EP) | A61M/25/00 |
| 59-80257 | 9/1984 | (JP) | A61M/25/00 |
| WO 90/14123 | 11/1990 | (WO) | A61M/25/00 |

\* cited by examiner

*Primary Examiner*—Sharon Kennedy
*Assistant Examiner*—Deborah Blyveis
(74) *Attorney, Agent, or Firm*—Larkin, Hoffman, Daly & Lindgren, Ltd.; Frederick W. Niebuhr, Esq.; Andrew D. Ryan, Esq.

(57) ABSTRACT

The invention relates to a radiopaque catheter tip and catheter assembly having radiopaque elements associated with a catheter. The preferred materials for the radiopaque elements are made of a 90% platinum and 10% nickel composite structure or a 90% platinum and 10% iridium composite structure.

17 Claims, 5 Drawing Sheets

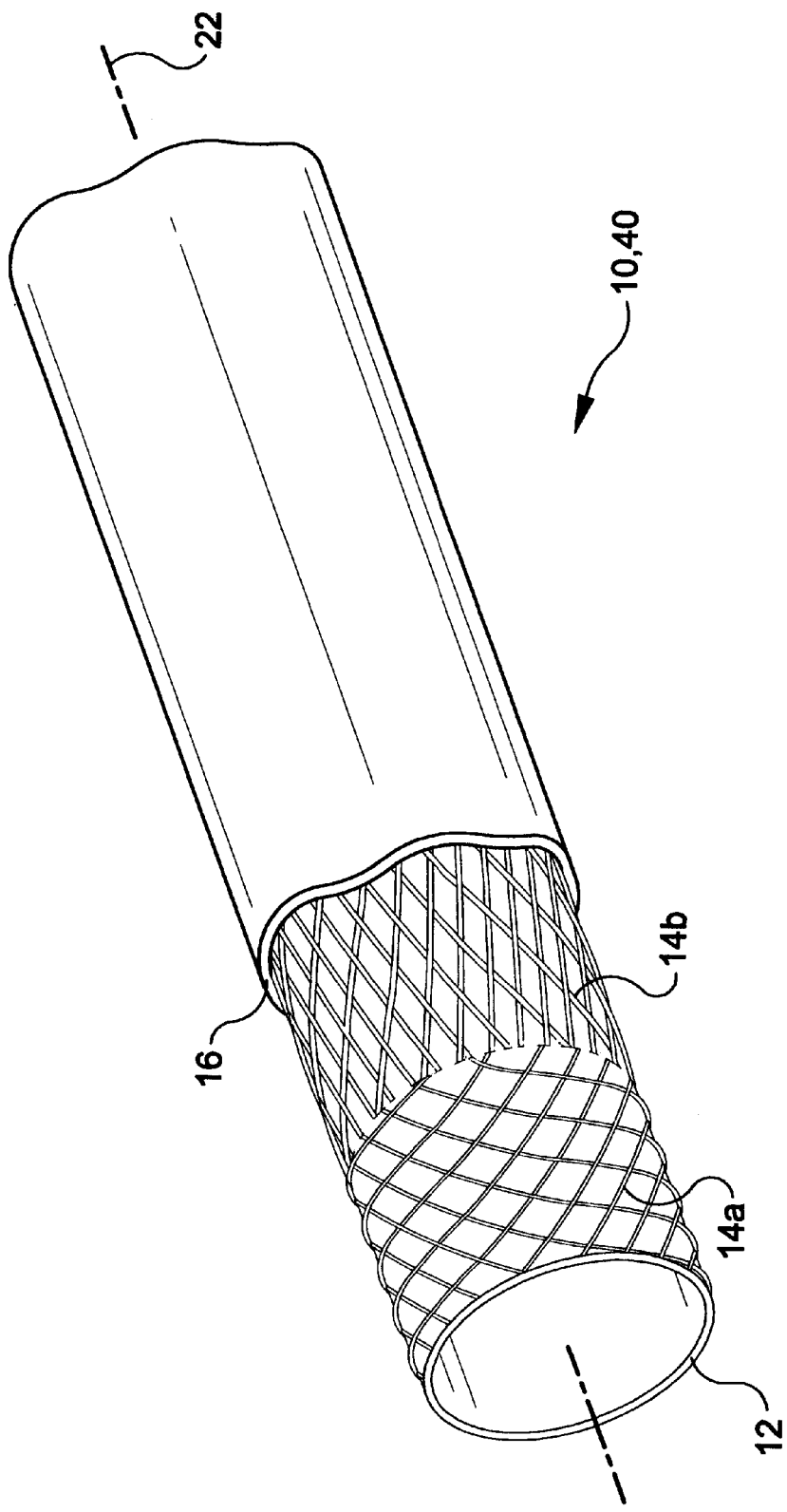

RADIOPAQUE CATHETER TIP

BACKGROUND OF THE INVENTION

The invention generally relates to a radiopaque catheter tip for use with a medical device.

Catheters are disclosed in U.S. Pat. Nos. 4,531,943; 4,547,193; 4,806,182; and 5,405,380. Catheter assemblies are disclosed in U.S. Pat. Nos. 4,646,742; 5,240,537; 5,364,357; 5,403,292; 5,545,151; and 5,599,325. Additional catheters are disclosed in U.S. Pat. Nos. 5,045,072; 5,171,232; and 5,221,270.

All references cited herein, including the foregoing, are incorporated herein in their entireties for all purposes.

SUMMARY OF THE INVENTION

The invention relates to a radiopaque catheter tip which may be joined to a medical device such as a catheter or may be manufactured in one-piece as part of the catheter. Use of the invention advantageously improves placement and imaging of a medical device during surgical procedures.

In sum, the invention relates to a radiopaque catheter tip and assembly. The assembly includes a first tube having a proximal end, a distal end, an inside diameter, an outside diameter, a first layer, a second layer and a third layer. The second layer includes one or more elongated elements having an average linear attenuation coefficients per unit of length in the range of about 70 to about 151.53 $cm^{-1}$ at 50 KeV disposed over at least a portion of the first layer. The third layer is disposed over the second layer. A second tube includes a proximal end, distal end, inside diameter and outside diameter. The first tube is positioned distal of the second tube and is associated with the second tube. The one or more elongated elements may be made of at least one of platinum, iridium, nickel, titanium or their alloys. The first layer may include at least one of a thermoplastic or polymer material, and the third layer may include a material having an average durometer hardness greater than the first layer. The first tube may have an average radiopacity per unit of length greater than the second tube. The first layer may be made of one of PTFE, high density polyethylene (HDPE), polyethylene (PE), Arnitel, nylon and the third layer may be made of one of polyether ester elastomer, Hytrel, Peba-nylon or nylon. The elongated elements may intersect at one or more locations and form an angle ranging from about 5 degrees to about 175 degrees. The elongated elements may be disposed in a generally helical pattern and form an elongated tube having a wall with openings between elements. The elongated elements may be formed in a generally helical coil. The first tube may have a length of from about 0.1 cm to about 20 cm. The elongated elements may be made of at least one of a wire, filament or ribbon. The elongated elements may have an average diameter or thickness between about 0.001 inches and about 0.005 inches.

The invention also relates to a radiopaque tip including a first layer having an outside surface, a proximal end, and a distal end. An intermediate layer includes one or more first elongated elements and one or more second elongated elements. The first elongated elements have an average linear attenuation coefficients per unit of length in the range of from about 70 to about 151.53 $cm^{-1}$ at 50 KeV and are disposed over a portion of the first layer. The second elongated elements have an average linear attenuation coefficients per unit of length less than about 100 $cm^{-1}$ at 50 KeV and are disposed over a portion of the first layer. A third layer of material is disposed over the intermediate layer. At least two of the layers are bonded together.

The invention also relates to a radiopaque tip including a tube including a plurality of layers, a proximal end, a distal end, a length, a lumen, and at least one radiopaque member having an average linear attenuation coefficients per unit of length in the range of from about 70 to about 151.53 $cm^{-1}$ at 50 KeV. The at least one radiopaque member is disposed over at least a portion of the length of the tube. The tube is adapted to be cut to a length and connected to a distal portion of a medical device. The at least one radiopaque member may be configured in a braided pattern such that openings are formed between the wires prior to a heating process.

The invention also relates to a radiopaque tip including a first layer of material forming a tube and a second layer. The second layer includes one or more radiopaque metal wires having an average thickness ranging from about 0.001 inches to about 0.005 inches that is formed in a pattern over at least a portion of the first layer of material. The first layer and the second layer are associated with one other and the radiopaque tip has sufficient flexibility for use in a body lumen when connected to a medical device.

The invention also relates to a radiopaque tip including a first layer having a diameter and a second layer disposed on the first layer. The second layer includes one or more first metal wires made of a first material having an atomic number greater than about 70 and less than about 83. The first metal wires form one or more angles between crossing wires. The one or more angles range from about 5 degrees to about 175 degrees. The second layer includes one or more second metal wires made of a second material having a lower average radiopacity than the first metal wires. The second metal wires form one or more angles between crossing wires. The one or more angles ranging from about 5 degrees to about 175 degrees. The one or more first metal wires are positioned distally of the second metal wires. A third layer is disposed on the second layer. The first, second and third layers are associated with at least one of the other. The first and second metal wires may overlap and be coaxial oriented over at least a portion of the catheter. The angle between crossing wires may decrease distally and the flexibility of the radiopaque catheter tip may increase distally. The angle between crossing wires may increases distally and the flexibility of the radiopaque catheter tip may decrease distally. The first and the second metal wires may be separated longitudinally or be separated radially apart from one another by a space or a material.

The invention also relates to a method of forming a radiopaque catheter tip including providing a first layer of material in the form of a tube; providing a second layer including one or more elongated elements having radiopaque characteristics; disposing the elongated elements over at least a portion of the first layer; providing a third layer of material; disposing the third layer over at least a portion of the elongated elements; applying radial compression to the layers; heating the layers at a temperature for a period of time to form a radiopaque tube having an end; providing a second tube having an end; and joining the end of the radiopaque tube to the end of the second tube. The method may further include prior to joining the end of the radiopaque tube to the end of a second tube, placing the radiopaque tube in about the same longitudinal axis and adjacent the second tube; applying shrink wrap tubing over at least a portion of the radiopaque tube, a joint portion between the radiopaque tube and the second tube, and the second tube; heating at least the joint portion to a condition such that the shrink wrap tubing radially compresses at least a portion of the radiopaque tube, a joint portion between the radiopaque tube and the second tube; and removing the shrink wrap tube. The method may further include prior to joining the end of the radiopaque tube to the end of a second tube, placing the radiopaque tube in about the same longitudinal axis and adjacent the second tube; applying shrink wrap tubing over at least a portion of the radiopaque tube, a joint portion between the radiopaque tube and the second tube, and the second tube; heating at least the joint portion at a temperature of about 230° to about 340° for about 20 seconds to about 80 seconds; and removing the shrink wrap tube. The method of forming a radiopaque catheter tip may further include after heating the layers, providing a length of the radiopaque tube; disposing the radiopaque tube on a mandrel; providing a length of the second tube; disposing the second tube on the mandrel tandemly adjacent the radiopaque tube; and heating the radiopaque tube and the second tube to a temperature for a period of time such that the materials bond and the two tubes are connected. The one or more layers may be heated above a glass transition temperature and less than a melting temperature.

The invention also relates to a tip including one or more elongated metal filaments embedded in polymer. The one or more elongated metal filaments include a metal having a linear attenuation coefficient per unit of length of from about 70 to about 151.53 $cm^{-1}$ at 50 KeV. The filaments may include at least one of platinum, tantalum, iridium, gold, bismuth, or alloys thereof. The tip may be disposed on a distal end of a catheter and have a greater flexibility than the distal end of the catheter. The one or more elongated filaments may be braided. The one or more elongated filaments may be coiled.

Still other objects and advantages of the present invention and methods of construction and use of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction and use, and its several details are capable of modification in various obvious respects, all without departing from the invention. Accordingly, the drawings and description are to be regarded as illustrative in nature, and not as restrictive.

BRIEF DESCRIPTION OF THE DRAWINGS

FIG. 9 is a schematic view of an embodiment of the radiopaque catheter tip and catheter assembly.

DETAILED DESCRIPTION OF THE PREFERRED EMBODIMENTS

Figure 1:
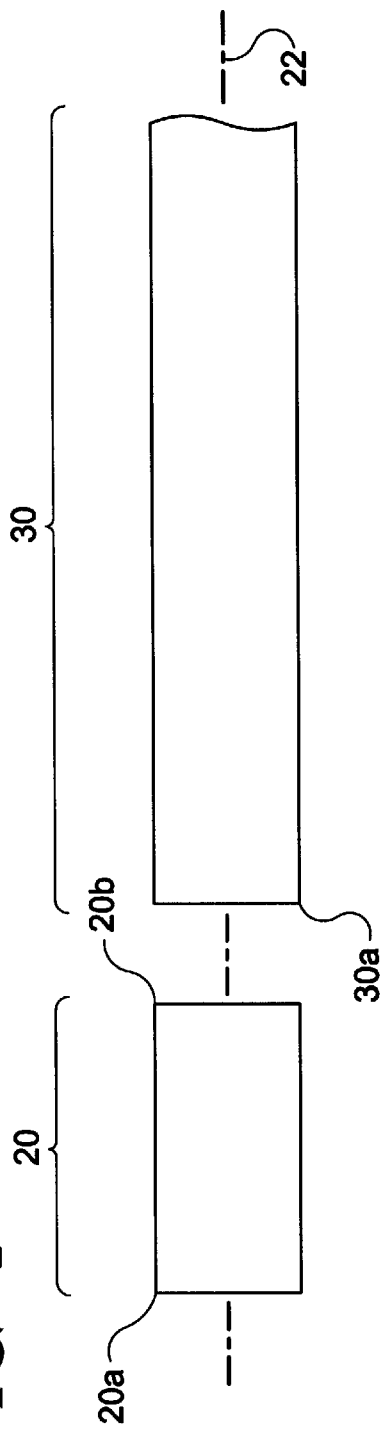
FIG. 1 illustrates a side view of a radiopaque catheter tip and a distal end of a catheter prior to bonding.

As shown in FIG. 1, an embodiment of the radiopaque catheter tip and catheter assembly 10 includes a first tube 20 and a second tube 30.

The first tube 20 (radiopaque catheter tip) has a proximal end 20b, a distal end 20a, an inside diameter, an outside diameter, a first inner layer 12, and a second layer 14a. The second layer 14, prior to heating of the layers, includes elongated elements 14a which are disposed in a pattern over a portion of the first inner layer 12. A third outer layer 16 may be disposed over the second layer 14. The first inner layer 12 includes a thermoplastic or polymeric material, and the third outer layer 16 includes thermoplastic or polymeric material having a durometer hardness preferably greater than the durometer hardness of the first layer 12. The materials in layers 12, 16 may include fillers or surface modifications. The first layer 12 may be made of PTFE and the third layer may be made of a polyether ester elastomer such as Arnitel. The first layer 12 may have an average thickness of about 0.002 inches and the third layer may have an average thickness of about 0.006 inches. The elongated elements 14a are preferably made of platinum, iridium, nickel, or titanium and have an average linear attenuation coefficients per unit of length in the range of about 70 to about 151.53 $cm^{-1}$ at 50 KeV. The elongated elements 14a are preferably disposed in a helical pattern and intersect at locations forming a braid angle α and an elongated tube structure with a wall and openings 18. The first tube 20 may have a length of from about 0.1 cm to about 20 cm. A preferred length may be about 2 mm to about 5 mm.

The second tube 30 has an inside and outside diameter about the same size as the inside and outside diameter of the first tube 20 where joined with the first tube 20. The second layer 14b of the second tube 30 includes elongated elements 14b disposed over a portion of a first inner layer 12. The elongated elements 14b are preferably disposed in a helical pattern and intersect at locations forming a braid angle θ and an elongated tube structure with a wall and openings 18.

Tube 20 may be made in various lengths, cut to a desired length, and then connected to an end of a second tube 30 to form the radiopaque catheter tip and catheter assembly 10. Tube 20 is generally positioned distal of the second tube 30 and is either directly connected to the second tube 30 or connected to one or more intermediate sections therebetween. The elongated elements 14a, 14b may be a wire, filament, or ribbon. The elements 14a, 14b may have an average diameter between about 0.001 inches and about 0.005 inches. The first tube 20 generally has an average radiopacity per unit of length greater than the second tube 30.

Figure 3:
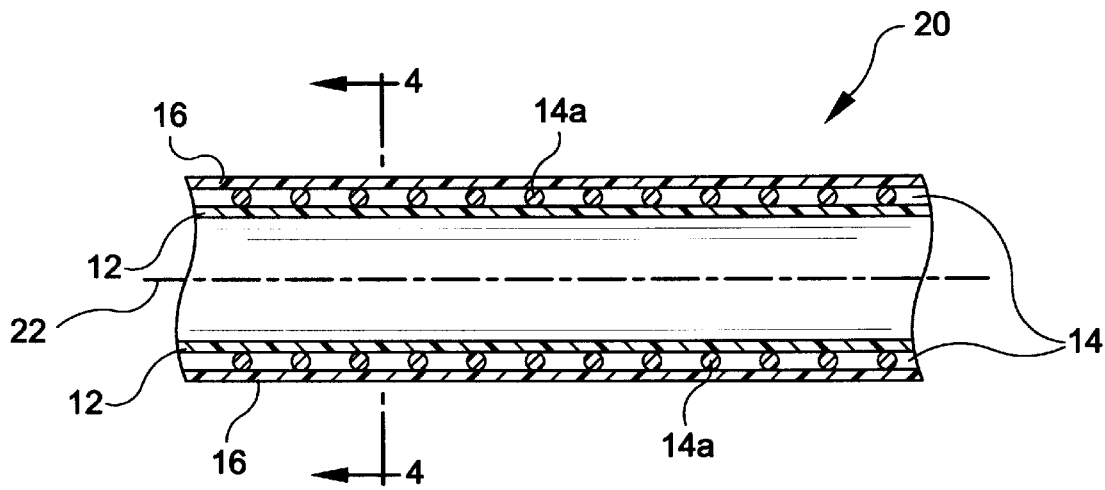
FIG. 3 illustrates a cross-sectional view of a radiopaque catheter tip and catheter assembly.
Figure 4:
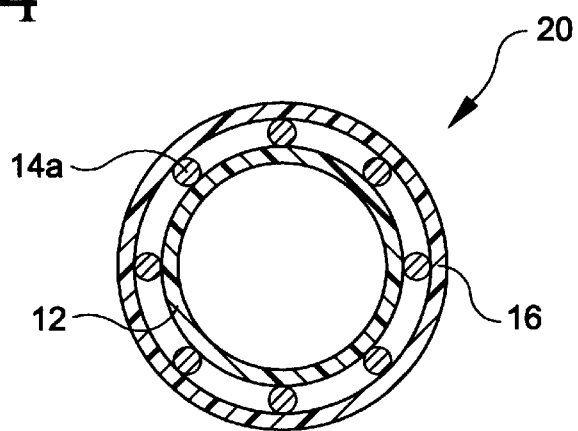
FIG. 4 illustrates space across-sectional end view of the radiopaque catheter tip and catheter assembly of FIG. 3.

FIGS. 3–4 show longitudinal and end cross-sections of an embodiment of a portion of the first tube 20 prior to heating, melting and bonding of the layers. Melting and bonding preferably occurs between adjacent materials and in the opening between the adjacent or intersecting elongated elements 14a. As the adjacent layers are heated above their respective glass transition temperatures, the elements 14a become further embedded in the layers. The second layer 14a is preferably made of a platinum/nickel or platinum/iridium composite wire structure and has a braid angle a ranging from about 100 to about 160 degrees, although other braid angles outside this range may be used to obtain a certain density of elements 14a over a length. In general, as the braid angle approaches 180 degrees, the density of the elements 14a is greatest.

Elements 14a preferably include certain material having atomic elements with sufficiently high atomic number and should be of a certain thickness to provide sufficient radiopacity for imaging in a body lumen. Radiopacity may be quantified by the atomic attenuation coefficient which is proportional to the linear attenuation coefficient and the atomic number of the absorber element. Radiopacity is generally proportional to the atomic number (number of electrons in the atom) of the material. Reference is made to linear attenuation coefficient described in U.S. Pat. No. 5,628,787.

Elements 14a may have atomic numbers ranging from about 56 to about 83 to provide sufficient radiopacity without excessive thickness, although, materials having atomic numbers ranging from about 70 to about 83 are preferred. Especially preferred elements 14a have atomic number greater than about 77 and less than about 83 and have a higher average radiopacity than the elements 14b. Preferably, elements 14a are made of about a 90% platinum and 10% nickel composite structure or about a 90% platinum and 10% iridium composite structure. Elongated elements 14a may be made of a radiopaque clad composite structure described in U.S. Pat. No. 5,630,840 and Titanium Alloy.

Preferred materials and their respective atomic numbers and linear attenuation coefficients are listed as follows:

| Element or Material | Atomic Number or Effective Atomic Number | Linear Attenuation Coefficient at 50 KeV, cm$^{-1}$ |
| --- | --- | --- |
| iridium | 77 | 151.53 |
| tantalum | 73 | 94.95 |
| platinum | 78 | 149.08 |
| gold | 79 | 140.12 |
| lead | 82 | 91.17 |
| bismuth | 83 | 82.12 |
| nickel | 28 | 21.98 |
| titanium | 22 | 5.46 |

The radiopaque catheter tip and catheter assembly 10, 40 may be made by various methods. For example, first tube 20 may be made by providing a first layer 12 of material in the form of a tube structure. A second layer 14 including one or more elongated elements 14a with certain radiopaque characteristics is disposed over at least a portion of the first layer 12. A third layer 16 of material may be disposed over at least a portion of the elongated elements 14a. Radial compression is applied to the layers 12, 14, 16. Heat is applied to the layers 12, 14, 16 at a temperature for a period of time to form a radiopaque tube 20 having an end 20b.

A preferred embodiment of the first tube 20 used in the radiopaque catheter tip and catheter assembly 10 includes a second layer 14a made of a wire about 0.002 inches in diameter which is braided over about a 0.094 inches core stock on a 16 carrier braiding machine. Use of braiders having between about 8 and 32 carriers are preferred, although, other sized braiders having more or less carriers are envisioned. The second layer 14a is removed from the core stock and then disposed over a first layer 12 made of PTFE tubing and then disposed on a steel mandrel (not shown) having about a 0.087 inches diameter. A third outer layer 16 made of Arnitel tubing with a 63 durometer is disposed over the second layer 14a. Other materials including various polymers and plastics may also be used. Heat shrink tubing 21 is disposed over layers 12, 14a, and 16 are heated in an oven for about 220 seconds at 480° F. After the layers 12, 14a, and 16 are cooled, the heat shrink tubing 21 is cut away and the mandrel is removed leaving a first tube 20 which may be cut to a desired length.

A second tube 30 having an end 30a is joined to the end 20b of the radiopaque tube 20. The joining method may include placing the radiopaque tube 20 adjacent to and in about the same longitudinal axis 22 as the second tube 30; applying shrink wrap tubing 21 over at least a portion of the radiopaque tube 20, over a joint portion 23, and over at least a portion the second tube 30; heating at least the area about the joint portion 23 at a temperature of about 230° to about 340° for about 20 seconds to about 80 seconds; and removing the shrink wrap tubing 21. A certain length of the radiopaque tube 20 along with the second tube 30 may be tandemly disposed on a mandrel (not shown). The radiopaque tube 20 and second tube 30 are heated to a temperature and for a period of time such that the two tubes 20, 30 melt together and are connected together forming a generally seamless connection and an assembly 10. Preferably, the one or more of the layers 12, 16 are heated above their respective glass transition temperature and less than their melting temperature. Thereafter, the assembly 10 is cooled and removed from the mandrel.

A preferred method of joining and forming assembly 10 may include providing a first tube 20 and bonding the same to a second tube 30. A generally short mandrel may be disposed in the end of the second tube 30 and the first tube 20 may also be disposed also on the mandrel adjacent the second tube 30. Heat shrink tubing 21 may be disposed over the two tubes 20, 30 and the area about the joint 23 may be heated using a bonding machine which holds the two tubes 20, 30 in a metal die or clamp and applies heat to the joint area. The bonding machine may include a two jaws made of beryllium and copper. The jaws have a hole drilled through the center, half through each side. The diameter of the hole in the jaw is equal to, or slightly less than the outside diameter of the outer tube, plus the total wall thickness of the FEP heat shrink. The width of the jaws are preferably between about 2 mm and about 10 mm. The jaws are individually heated using a cartridge heater that is controlled with a thermocouple. The jaws are preferably heated to a temperature of about 240 degrees C. to about 280 degrees C., for about 40 seconds at about 30 psi. Thereafter, the heat shrink tubing 21 may be cut away; and the assembly 10 may be removed from the mandrel.

Figure 2:
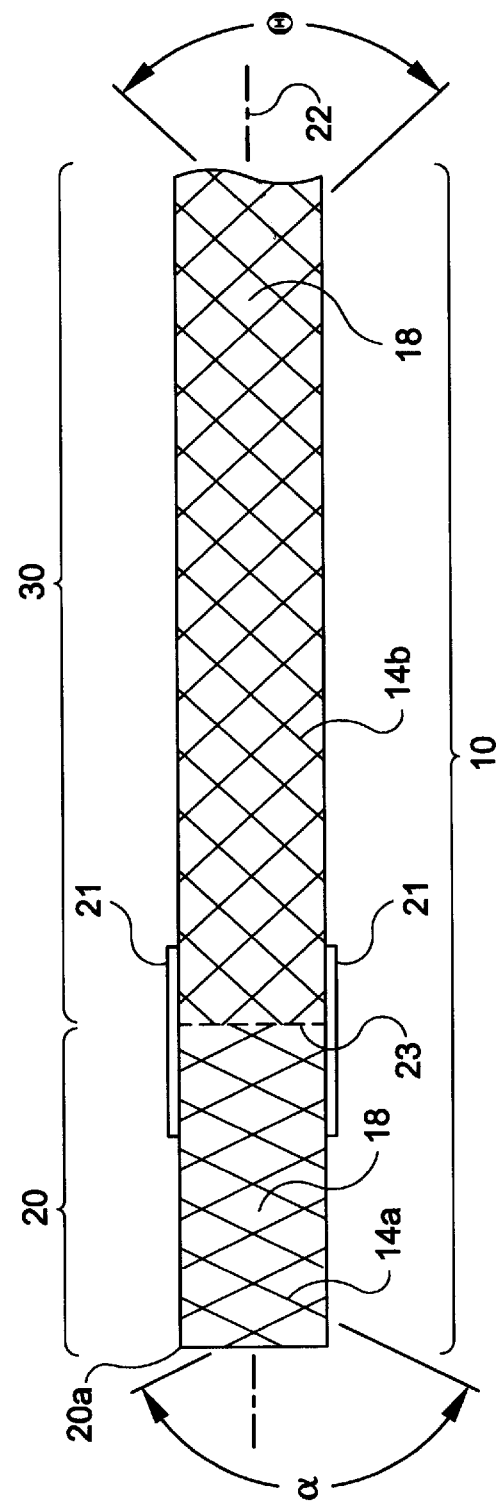
FIG. 2 illustrates a side view of a radiopaque catheter tip and catheter assembly (outer layer not shown)
Figure 5:
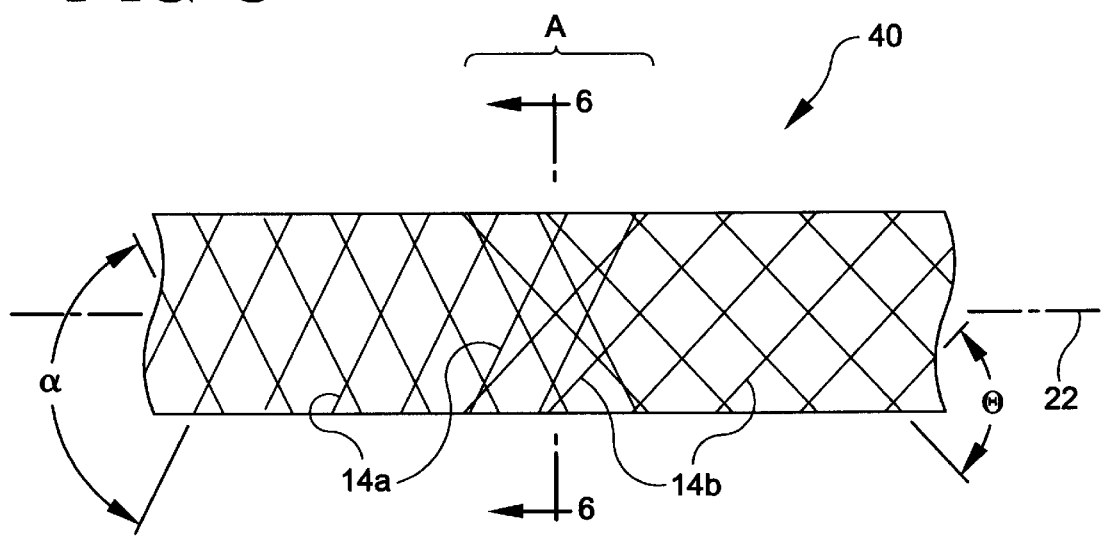
FIG. 5 illustrates a side view of an embodiment of a radiopaque catheter tip and catheter assembly with overlapping elongated element portions (outer layer not shown)
Figure 6:
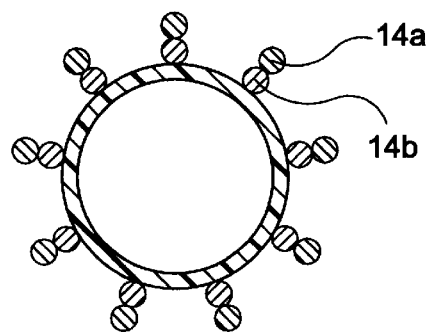
FIG. 6 illustrates an end cross-sectional view of the radiopaque catheter tip and catheter assembly of FIG. 5.
Figure 7:
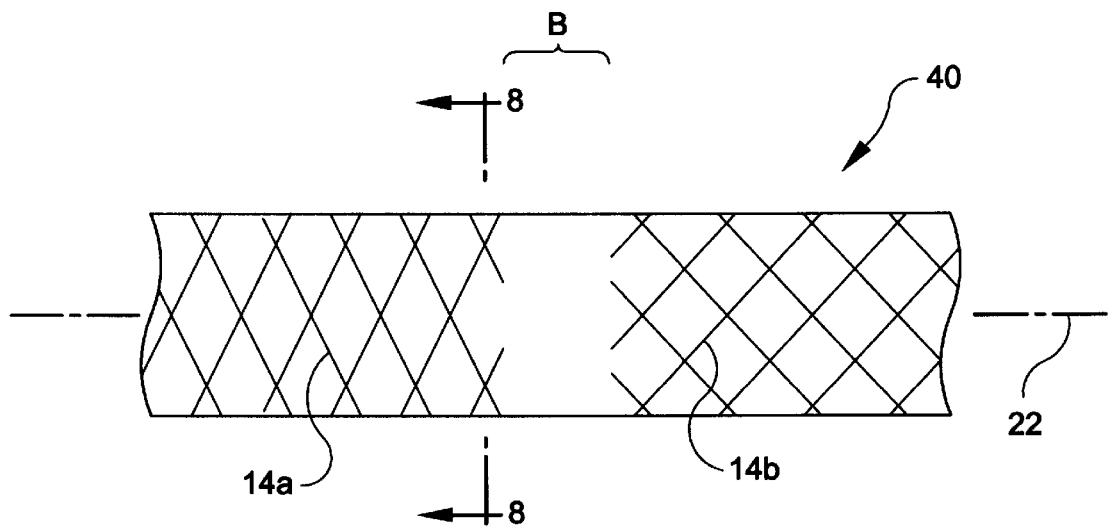
FIG. 7 illustrates a side view of an embodiment of a radiopaque catheter tip and catheter assembly with spacing between elongated element portions (outer layer not shown)

As shown in FIGS. 5–8, another embodiment, radiopaque catheter tip and catheter assembly 40 may be made in one length as opposed to joining two lengths of tubing 20, 30 to form assembly 10 as shown in FIGS. 1–2. Although, FIGS. 5–8 are shown without outer layer 16, preferred embodiments include an outer layer 16. Preferably, the radiopaque catheter tip and catheter assembly 40 includes a one-piece first layer 12, a second layer 14 including one or more elongate elements 14a, 14b preferably having a certain range of radiopacity and formed in a braided pattern on the first layer 12, and a third outer layer 16. As shown in FIG. 5, radiopaque elements 14a may overlap second radiopaque elements 14b and be generally coaxial along portion A. Alternatively, radiopaque elements 14a may be separated from second radiopaque elements 14b by portion B as shown in FIG. 7. Portions A and B preferably range from about 1 mm to about 5 mm in length.

Figure 8:
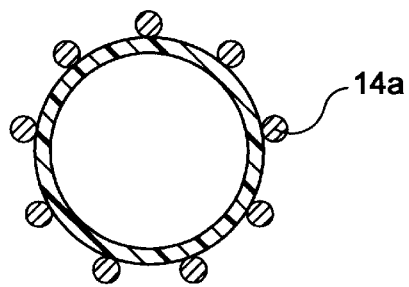
FIG. 8 illustrates a cross-sectional end view of the radiopaque catheter tip and catheter assembly of FIG. 7.

Preferably, the second layer 14 includes one or more wires 14a made of a first metal material formed in a first pattern, and one or more second metal wires 14b made of a second material formed in a second pattern. The first metal wires 14a are preferably positioned at a distal portion of the radiopaque catheter tip and catheter assembly 40. The first braid may have a braid angle ranging from about 100 degrees to about 160 degrees and the second braid may have a braid angle ranging from about 100 degrees to about 160 degrees. FIGS. 6 and 8 show end views of FIGS. 5 and 7 respectively. Braiding when utilized, can be performed in the manner disclosed in U.S. Pat. No. 4,655,771.

Reference is made to FIG. 9 showing a schematic view of an embodiment of the radiopaque catheter tip and catheter assembly 10, 40 of which various embodiments and sizes are envisioned in about the 3 French to about 34 French range.

Preferably, the tip will be a soft, symetrically deformable member for decreasing the likelihood of injury to body tissue, and may have properties such as described in U.S. Pat. No. 4,531,943.

Although the present invention has been described with reference to preferred embodiments, those skilled in the art will recognize that changes can be made in form and detail without departing from the spirit and scope of the invention.

It will be evident from considerations of the foregoing that the Radiopaque Catheter Tip may be constructed using a number of methods and materials, in a wide variety of sizes and styles for the greater efficiency and convenience of a user.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

What is claimed is:

1. A radiopaque catheter tip and assembly comprising:

a first tube including a proximal end, a distal end, an inside diameter, an outside diameter, a first layer, a second layer including one or more elongated elements having an average linear attenuation coefficient per unit of length in the range of about 70 to about 151.53 cm$^{-1}$ at 50 KeV disposed over at least a portion of the first layer, and a third layer disposed over the second layer; and a second tube including a proximal end, distal end, inside diameter and outside diameter;

wherein the first tube is positioned distally of the second tube and is associated with the second tube.

2. The radiopaque catheter tip and assembly of claim 1 wherein the one or more elongated elements are made of a metal selected from the group of metals consisting of: platinum, iridium, gold, bismuth, tantalum, and an alloy including one of platinum, iridium, gold, bismuth, and tantalum.

3. The radiopaque catheter tip and assembly of claim 1 wherein the first layer comprises at least one of a thermoplastic or polymer material, and the third layer comprises a material having an average durometer hardness greater than the first layer.

4. The radiopaque catheter tip and assembly of claim 1 wherein the first tube has an average radiopacity per unit of length greater than the second tube.

5. The radiopaque catheter tip and assembly of claim 1 wherein the first layer is made of one of polytetrafluoroethylene (PTFE), high density polyethylene (HDPE), polyethylene (PE), or Arnitel and the third layer is made of one of polyether ester elastomer, Peba-nylon or nylon.

6. The radiopaque catheter tip and assembly of claim 1 wherein the one or more elongated elements intersect at one or more locations and form an angle ranging from about 5 degrees to about 175 degrees.

7. The radiopaque catheter tip and assembly of claim 1 wherein the one or more elongated elements are disposed in a generally helical pattern and form an elongated tube having a wall with openings between elements.

8. The radiopaque catheter tip and assembly of claim 1 wherein the first tube has a length of from about 0.1 cm to about 20 cm.

9. The radiopaque catheter tip and assembly of claim 1 wherein the one or more elongated elements is at least one of a wire, filament or ribbon.

10. The radiopaque catheter tip and assembly of claim 9 wherein the one or more elongated elements has an average diameter or thickness between about 0.001 inches and about 0.005 inches.

11. A radiopaque tip comprising:

a first layer having a diameter;

a second layer disposed on the first layer and including one or more first metal wires made of a first material having an atomic number greater than about 70 and less than about 83, the first metal wires forming one or more angles between crossing wires, the one or more angles ranging from about 5 degrees to about 175 degrees, and one or more second metal wires made of a second material having a lower average radiopacity than the first metal wires, the second metal wires forming one or more angles between crossing wires, the one or more angles ranging from about 5 degrees to about 175 degrees, the one or more first metal wires positioned distally of the second metal wires;

a third layer disposed on the second layer; and wherein each of the first, second and third layers is associated with at least one of the other, the angle between crossing wires decreases distally, and the flexibility of the radiopaque catheter tip increases distally.

12. A radiopaque tip comprising:

a first layer having a diameter;

a second layer disposed on the first layer and including one or more first metal wires made of a first material having an atomic number greater than about 70 and less than about 83, the first metal wires forming one or more angles between crossing wires, the one or more angles ranging from about 5 degrees to about 175 degrees, and one or more second metal wires made of a second material having a lower average radiopacity than the first metal wires, the second metal wires forming one or more angles between crossing wires, the one or more angles ranging from about 5 degrees to about 175 degrees, the one or more first metal wires positioned distally of the second metal wires;

a third layer disposed on the second layer; and wherein each of the first, second and third layers is associated with at least one of the other, the angle between crossing wires increases distally, and the flexibility of the radiopaque catheter tip decreases distally.

13. A combination of a medical device and tip, comprising:

a polymeric first layer forming a tube; and a second layer disposed on the first layer and including a fit layer portion formed of a first metal having a first average radiopacity, the second layer further including a second layer portion disposed proximally of the first layer portion and formed of a second metal having a second average radiopacity less than the first average radiopacity;

wherein the first portion of the layer consists essentially of a plurality of first wires made of the first metal, the second portion of the second layer consists essentially of a plurality of second wires made of the second metal said first wires cross one another to form angles within the range from about 5 degrees to about 175 degrees, and said second wires cross one another to form angles within the range from about 5 degrees to about 175 degrees; and wherein in angle between said crossing first wires is greater than the angle between said crossing second wires.

14. The combination of claim 13 further including:
a polymeric third layer disposed on the second layer.

15. The combination of claim 13 wherein:
said first and second portions of the second layer are disposed in axially spaced apart relation to one another.

16. The combination of claim 13 wherein:
said first linear attenuation coefficient is at least 70 cm.$^{-1}$ at 50 KeV.

17. A combination of a medical device and tip, comprising:

a polymeric first layer forming a tube; and a second layer disposed on the first layer and including a first layer portion formed of a first metal having a first average radiopacity, the second layer further including a second layer portion disposed proximally of the first layer portion and formed of a second metal having a second avenge radiopacity less to the first average radiopacity;

wherein the first portion of the second layer consists essentially of a plurality of first wires made of the first metal, the second portion of the second layer consists essentially of a plurality of second wires made of the second metal, said first wires cross one another to form angles within the range from about 5 degrees to about 175 degrees, and said second wires cross one another to form angles within the range form about 5 degrees to about 175 degrees; and wherein the angle between said crossing second wires is greater than the angle between said crossing first wires.

* * * * *